| (12) | United States Patent | (10) Patent No.: | US 8,235,964 B2 |
|---|---|---|---|
| | Perneborn | (45) Date of Patent: | Aug. 7, 2012 |

(54) PANT-LIKE ABSORBENT ARTICLE AND A METHOD FOR MAKING IT

(75) Inventor: Robert Perneborn, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 573 days.

(21) Appl. No.: 12/282,354

(22) PCT Filed: Apr. 25, 2006

(86) PCT No.: PCT/SE2006/000480

§ 371 (c)(1), (2), (4) Date: Sep. 10, 2008

(87) PCT Pub. No.: WO2007/123445

PCT Pub. Date: Nov. 1, 2007

(65) Prior Publication Data

US 2009/0043275 A1      Feb. 12, 2009

(51) Int. Cl.
*A61F 13/15* (2006.01)

(52) U.S. Cl. ............... 604/396; 604/392; 604/385.11; 604/385.201

(58) Field of Classification Search .......... 604/389–392, 604/394, 385.201, 385.11, 396
See application file for complete search history.

(56) References Cited

U.S. PATENT DOCUMENTS

| 4,670,012 | A | | 6/1987 | Johnson | |
|---|---|---|---|---|---|
| 5,695,488 | A | * | 12/1997 | Sosalla | .............. 604/385.24 |
| 5,855,574 | A | * | 1/1999 | Kling et al. | ............... 604/392 |
| 6,030,373 | A | * | 2/2000 | VanGompel et al. | ......... 604/386 |
| 6,113,717 | A | | 9/2000 | Vogt et al. | |
| 6,328,725 | B2 | | 12/2001 | Fernfors | |
| 6,579,275 | B1 | * | 6/2003 | Pozniak et al. | ............... 604/390 |
| 6,648,871 | B2 | * | 11/2003 | Kusibojoska et al. | ........ 604/392 |
| 6,849,067 | B2 | * | 2/2005 | Fletcher et al. | ............... 604/389 |

(Continued)

FOREIGN PATENT DOCUMENTS

EP          1 470 808 A2      10/2004

(Continued)

OTHER PUBLICATIONS

International Search Report for PCT/SE2006/000480, completed Nov. 8, 2006.

(Continued)

*Primary Examiner* — Lynne Anderson
*Assistant Examiner* — Peter S Vasat
(74) *Attorney, Agent, or Firm* — Buchanan Ingersoll & Rooney PC (57) ABSTRACT

A pant-type absorbent article having a first body panel and a second body panel, the first and second body panels being interconnected by side panels. The respective side panel is formed by a bridge member having a first longitudinal edge portion attached to the first body panel and a second longitudinal edge portion attached to the second body panel, the bridge before use of the article being folded in an accordion-like fashion and can be extended and unfolded when the article is to be used so as to form the side panels of the article. In one embodiment at least one of the bridge members is refastenably attached to one body panel, wherein a first fastening member is arranged on the bridge member at or close to one longitudinal edge portion thereof and a complementary second fastening member is arranged on the respective body panel.

15 Claims, 4 Drawing Sheets

U.S. PATENT DOCUMENTS

| | | | |
|---|---|---|---|
| 2001/0034512 A1 | 10/2001 | Karlsson et al. | |
| 2002/0138062 A1 | 9/2002 | Kuen et al. | |
| 2002/0174931 A1* | 11/2002 | Couillard et al. | 156/66 |
| 2003/0062121 A1 | 4/2003 | Franklin et al. | |
| 2004/0039364 A1* | 2/2004 | Karami | 604/391 |
| 2004/0092903 A1* | 5/2004 | Olson et al. | 604/389 |

FOREIGN PATENT DOCUMENTS

| | | |
|---|---|---|
| EP | 1719484 A1 | 11/2006 |
| GB | 2245149 A | 1/1992 |
| JP | 4-828 U | 1/1992 |
| JP | 9-511426 A | 11/1997 |
| JP | 2005-253487 A | 9/2005 |
| JP | WO 2005/079720 A1 | 9/2005 |
| JP | 2006-333 A | 1/2006 |
| WO | WO 95/27461 A1 | 10/1995 |
| WO | WO 95/27462 A1 | 10/1995 |
| WO | WO 97/23180 A1 | 7/1997 |
| WO | WO 00/35401 A1 | 6/2000 |
| WO | WO 01/87204 A1 | 11/2001 |
| WO | WO 03/024377 A2 | 3/2003 |
| WO | WO 03/057116 A1 | 7/2003 |

OTHER PUBLICATIONS

International Preliminary Report on Patentability for PCT/SE2006/000480, completed Jun. 30, 2008.

English language translation of the Notice of Reasons for Rejection mailed Apr. 19, 2011 by the Japanese Patent Office in corresponding Japanese Patent Application No. 2009-507616.

* cited by examiner

PANT-LIKE ABSORBENT ARTICLE AND A METHOD FOR MAKING IT

TECHNICAL FIELD

The present disclosure refers to a pant-type absorbent article, such as a pant diaper, training pant, swim pant, sanitary pant or incontinence pant. The disclosure further refers to a method for making the absorbent article.

BACKGROUND

Pant-type absorbent articles have a defined waist opening and a pair of leg openings and are pulled onto the body of the wearer by inserting the legs into the leg openings and pulling the article up over the waist. They are usually provided with various elastic elements so that they can conform to the body of the user and provide a comfortable fit. Examples of such pant-type absorbent articles are pant diapers, sanitary pants and incontinence pants worn by incontinent adults. They comprise a first body panel and a second body panel, forming the front and back panels of the pant. The first and second body panels are joined to each other along lateral edges to form side connections. A crotch panel is provided between the first and second body panels. The crotch panel can be integral with either one or both panels or can be provided as a separate part joined to the first and second body panels.

Pant-type absorbent article often do not have a refastening mechanism that allows the garment to be easily removed after use or to be adjusted during use. However there are known through various prior art documents such refastenable pant-type absorbent articles.

WO 95/27462 discloses a pant diaper having releasable and refastenable fastening means along the lateral edges of the front and back panels for joining the front and back panels together along the sides thereof. The refastenable fastening means replaces a permanent side seam.

WO 01/87204 discloses an absorbent garment with a refastenable side seam. Complementary fasteners are applied at the front and the back panels on the wearer facing side and one of the complementary fasteners is applied to the panel in a C-folded configuration such that a lap seam is formed.

WO 03/024377 discloses a refastenable absorbent garment comprising a plurality of fastener pieces spaced along the side edges forming refastenable side seams of the garment. Cuts may be provided in the body panel webs between the fastener pieces.

WO 03/057116 discloses a refastenable absorbent garment having a fastening tab hingedly connected to the body facing side of a first body panel. The fastening tab is hinged and folded over along a folding line adjacent a lateral side edge of the body panel and is in the folded over state releasably fastened to the body facing side of the opposite body panel. No overlapping side seams between the first and second body panels are provided along their joined side edges.

WO 00/35401 discloses a refastenable pant diaper having a pair of side panels in a first waist region, said side panels being provided with fastening components disposed on the wearer facing surface. The fastening components are adapted to releasably engage with mating fastening components disposed in a second waist region on the garment facing side.

Although several different types of refastenable pant-type absorbent articles are already known, there still exists a need for alternative solutions.

OBJECT AND SUMMARY

The present disclosure aims at providing a pant-like absorbent articles such as a pant diaper, a training pant, a swim pant, a sanitary pant or incontinence pant. The article should be configured in a space-saving manner before use and be simple to manufacture in a cost efficient way.

According to embodiments of the invention there is provided a pant-type absorbent article comprising a first body panel having a body facing side and a garment facing side and a second body panel having a body facing side and a garment facing side. The first and second body panels being interconnected by side panels, the respective side panel being formed by a bridge member having a first longitudinal edge portion attached to the first body panel and a second longitudinal edge portion attached to the second body panel. Before use of the article the bridge member is folded in an accordion-like fashion in the longitudinal direction of the article and can be extended and unfolded when the article is to be used so as to form said side panels of the pant-type absorbent article.

In one aspect of the disclosure at least one of said bridge members is refastenably attached to the first and/or second body panel, wherein a first fastening member is arranged on said bridge member at or close to one longitudinal edge portion thereof and a complementary second fastening member is arranged on the respective body panel.

According to one embodiment the first and second fastening members are hook-and-loop type fasteners. In a preferred embodiment at least part of the second portion of the first fastening member is of a loop material and the second fastening member comprises a hook material.

In a further aspect the unattached portion of the first fastening member before use is Z-folded.

According to one embodiment at least a part of the first fastening member is elastic.

In a further embodiment the bridge member has an extension in the transverse direction of the article of at least 1 cm, preferably at least 2 cm and more preferably at least 3 cm as seen as the distance between its lateral edges.

According to one embodiment that the length of the first fastening member as seen in longitudinal direction (y) is at least 75% of the length of the respective lateral edge of the first body panel near which it is attached, preferably at least 90% of said length and more preferably substantially equal to said length.

In one aspect of the disclosure the second fastening member is attached to the respective body panel at a distance, b, of at least 2 mm, preferably at least 3 mm, inside the lateral side edge of said body panel. This will form a grip tab which makes it easier to open the refastenable fastening means.

In a further embodiment the width in the transverse direction (x) of the second fastening member is at least 3 mm, preferably at least 5 mm, and the length in longitudinal direction (y) is substantially equal to the length of the first fastening member.

In one aspect of the disclosure the accordion-like folds are held together, before the intended use of the article, by easily breakable seals.

According to a further embodiment the bridge member has both of its longitudinal edge portions fixedly attached to the respective side panel.

The disclosure further refers to a method of making method of making side panels in a pant-like absorbent article, said article having a longitudinal and transverse direction, said method comprising the steps of:

aligning a plurality of article blanks in a transverse direction, each article blank including first body panel and second body panel, wherein adjacent blanks are joined between their first body panels and between their second body panels at intended lines of separation, said article blanks having a body facing side and a garment facing side in its intended use as absorbent article;

feeding a bridge forming material to each of the first body panels, to the intended body facing side thereof, said bridge forming material being folded in an accordion-like fashion, applying said bridge forming material to each of the first body panel with the accordion-like folds extending in a substantial longitudinal direction of the article, bonding a portion of the bridge forming material to or adjacent the intended line of separation between adjacent first body panels, while the rest of the accordion-like folded bridge forming material is left unbonded, said unbonded portion having a longitudinal edge portion, folding the article blanks along a central transverse folding line and bonding the longitudinal edge portion of the accordion-like folded bridge forming material to the second body panel of the same article blank;

cutting the folded blanks along the intended line of separation to form pant-like absorbent articles therefrom;

or alternatively cutting the blanks along the intended lines of separation before folding them.

According to one embodiment said wing-forming material is provided with two accordion-like folded portions being the mirror image of each other and being interconnected by a connecting portion, wherein said connecting portion is bonded to adjacent first body panels on either sides of the intended line of separation there between, so that after cutting along the intended line of separation the connecting portion will be cut thus leaving each first body panel with an accordion-like folded portion attached thereto.

A further embodiment the invention refers to making refastenable pant-like absorbent articles, wherein the longitudinal edge portion of the accordion-like folded bridge forming material is provided with a first fastening member of a refastenable fastening means;

before folding the article blanks along their central transverse folding line bonding a second fastening member of said refastenable fastening means to the second body panel of each article blank;

folding the article blanks along their central transverse folding line so that the first fastening member is brought in contact with the second fastening member bonded to the second body panel of the same blank to provide a refastenable bonding of the accordion-like folded bridge forming material to the second body panel.

In a further embodiment the accordion-like folds are bonded together by easily breakable seals.

DEFINITIONS

Pant-Type Absorbent Article

Pant-type absorbent articles have a defined waist opening and a pair of leg openings and are pulled onto the body of the wearer by inserting the legs into the leg openings and pulling the article up over the waist. Examples of such pant-type absorbent articles are pant diapers, sanitary pants and incontinence pants worn by incontinent adults. Pant-type absorbent articles usually comprise a front body panel and a back body panel, which are joined to each other along two opposite longitudinal side edges to define a waist-opening and a pair of leg-openings. The pant-type absorbent article further comprises a crotch portion in the part of the article that in use is intended to extend through the wearer's crotch area, between the legs. The absorbent article is intended to be placed against the skin of the wearer to absorb and contain body exudates, like urine, faeces and menstrual fluid. The invention mainly refers to disposable absorbent articles, which means articles that are not intended to be laundered or otherwise restored or reused as absorbent articles after use.

Refastenable and Releasable Attachment

The term "refastenable" refers to a releasable attachment of two elements, thus the attachment may be separated and subsequently reattached without substantial permanent deformation or rupture. "Releasable attachment" refers to elements that are connected such that the elements tend to remain connected in the absence of a separation force being applied to one or both of the elements, and that the elements being capable of separation without substantial permanent deformation or rupture. The required separation force should typically be beyond that encountered while wearing the article.

Fixedly Attached

The term "fixedly attached" refers to two or more elements being attached to each other so that they are not intended to be separated or disconnected during normal use of the absorbent article.

Hook-and-Loop Fastener

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook-and-loop fasteners are for example available from Velcro, USA.

BRIEF DESCRIPTION OF THE FIGURES

The invention will in the following be closer described with reference to an embodiment, to which it is not limited, shown in the accompanying drawings.

DESCRIPTION OF PREFERRED EMBODIMENTS

An embodiment of the invention refers to pant-type absorbent articles 10, which have a defined waist opening 14 and a pair of leg openings 15 and which are pulled onto the body of the wearer by inserting the legs into the leg openings and pulling the article up over the waist. Examples of such pant-type absorbent article are pant diapers, training pants, swim pants, sanitary pants and incontinence pants worn by incontinent adults. The article will in the following be referred to as a "pant diaper". The article has a longitudinal direction x and a transverse direction y.

The pant diaper comprises a first body panel 16, which in the embodiment shown in the drawings is the part of the article that in use is intended to extend over the back and the rear hip area of the wearer. The article also comprises a second body panel 17, which in the shown embodiment is the part of the pant diaper that in use is intended to extend over the stomach and front hip area of the wearer. It is understood that in other embodiments the first body panel 16 may be the front body panel and the second body panel 17 may be the back body panel. The first and second body panels refer to certain areas of the article and may be continuous with and of the same material as other areas of the article or alternatively be of separate pieces of material joined to other areas of the article. The crotch portion 18 of a pant diaper article is the part of the diaper that in use is intended to extend through the wearer's crotch area, between the legs. An absorbent core 11 is disposed in the crotch portion 18 and extends into the front and back body panels 16 and 17. The absorbent core is disposed between an inner coversheet 12 and an outer coversheet 13.

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wet-laid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

The "outer coversheet" refers to the material forming the outer cover of the absorbent article. The outer coversheet may be the same or different in different parts of the absorbent article. At least in the area of the absorbent core the outer coversheet comprises a liquid impervious material a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises a nonwoven material on at least the garment-facing surface thereof.

The "absorbent core" is the absorbent structure disposed between the two coversheets of the absorbent article in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

The first and second body panels 16 and 17 or those parts thereof that are located outside the absorbent core region may have different material composition than the crotch portion 18. Thus according to one embodiment the areas of the first and second body panels 16 and 17 which are located outside the absorbent core region may be composed of for example a laminate material having a body facing side and a garment facing side, while a liquid impervious outer coversheet and/or a liquid pervious inner coversheet only is present in the absorbent core region. In other embodiments the inner and outer coversheets are the same in the first and second body panels 16 and 17 as well as in the crotch region 18. The first and second body panels 16 and 17 each have a pair of first lateral edges 19, 21 and second lateral edges 20, 22, respectively, and a transverse edge 23 and 24, respectively.

The lateral side edges of the first 16 and second body panels 17 are interconnected by side panels 25, wherein the diaper assumes a pant-like shape having the aforementioned waist opening 14 and leg openings 15. Each side panel 25 is formed from a bridge member 26 having one third lateral edge portion 27 fixedly attached to or near a lateral edge of the first or second body panel 16 or 17 on the body facing side thereof. At or close to the opposite fourth lateral edge portion 28 of the bridge member 26 a first fastening member 29 of refastenable fastening means is provided, for example mechanical fastening means like hook-and-loop fasteners, or adhesive fasteners. A complementary second fastening member 30 is arranged on the opposite body panel 17 or 16 on the body facing side thereof.

In an alternative embodiment (not shown) the bridge member 26 has both of its longitudinal edge portions fixedly attached to the respective side panel. In that case the pant article is not refastenable. In other embodiments only one of the bridge members 26 is refastenable, while the other bridge member has both longitudinal edge portions fixedly attached to the respective side panel. In still further embodiments both longitudinal edge portions of the bridge member is refastenably attached to the respective body panel.

The waist opening 14 and at least a part of the leg openings 15 are elasticized. The elastification is usually accomplished by a plurality of elastic members 31, such as elastic threads, which are contractably affixed between the outer coversheet 13 and the inner coversheet 12. Alternatively elastic materials, such as elastic laminates, may be used to form the first 16 and/or second body panels 17 in those areas where elasticity is desired.

The second fastening member 30 is, according to the embodiment shown in the drawings, fixedly attached to the body facing side of the second body panel 17, which in this case is the front body panel. The attachment 23 may be accomplished by gluing, ultrasonic welding, thermobonding or the like. In an alternative embodiment the second fastening member 30 is fixedly attached to the back body panel 16. The second fastening member 30 is attached adjacent or close to the respective first and second lateral side edge 21, 22 of the second body panel 17. Preferably it is attached a distance, b, (FIG. 3) at least 3 mm and preferably at least 5 mm inside the said lateral side edge, so that a grip tab is formed, which makes it easier to open the refastenable fastening means.

In a preferred embodiment the first and second fastening members 29 and 30 are complementary hook-and-loop fasteners.

According to one embodiment the second fastening member 30 is of a hook material, while the first fastening member 29 is of a loop material. The entire, a substantial part of or only a small part of the bridge member 26 may be of a loop material, for example a nonwoven material. "A substantial part" refers to at least 50% of the surface area of the bridge member. Making a substantial part of the bridge member 26 of loop material makes it possible to adjust the length of the side panels 25 in the transverse direction, x. However in other embodiments less than 50% of the surface area of the bridge member is of loop material.

In an alternative embodiment the first fastening member 29 is a hook member fixedly attached to the bridge member 26 at its fourth lateral edge portion 28. The second fastening member 30, the loop portion, may then be formed by the body facing side, i.e., the inner coversheet 12, of the respective body panel.

According to a further embodiment at least a part of the bridge member 26 is of an elastic material, such as an elastic nonwoven or an elastic laminate material. In this way elastic side panels 25 are formed.

Figure 1:
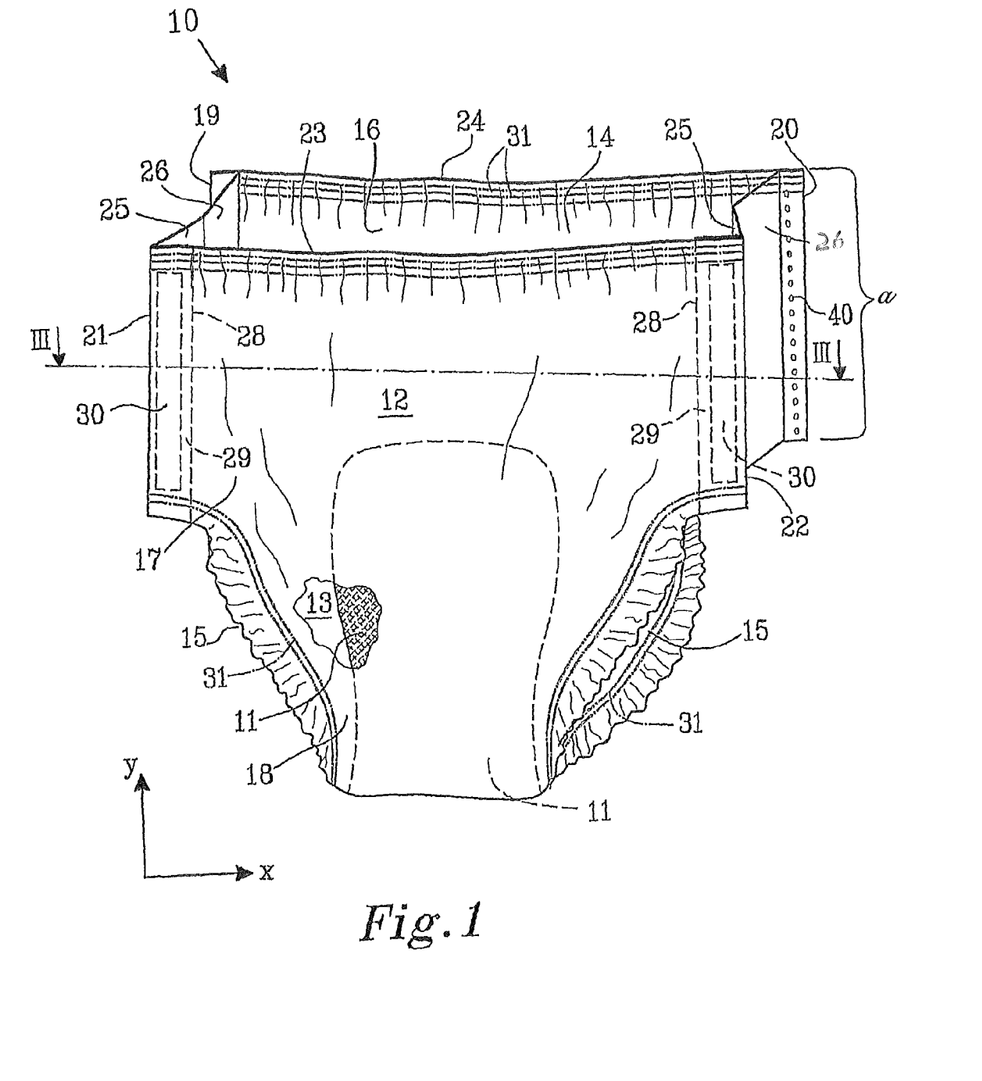
FIG. 1 shows a refastenable pant diaper.
Figure 2:
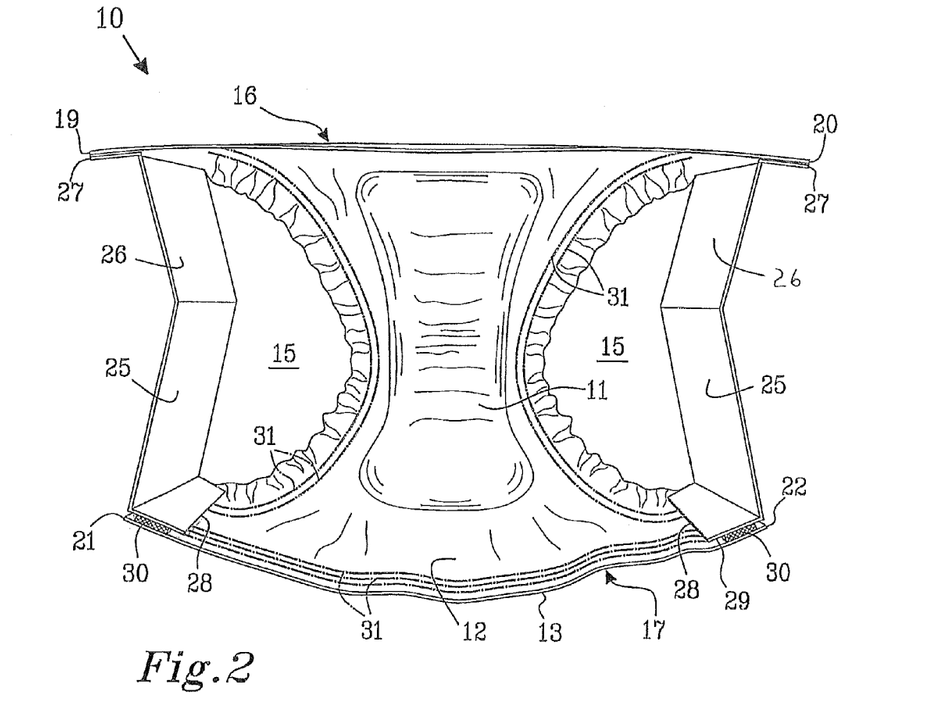
FIG. 2 is a view from above of the pant diaper.
Figure 3:
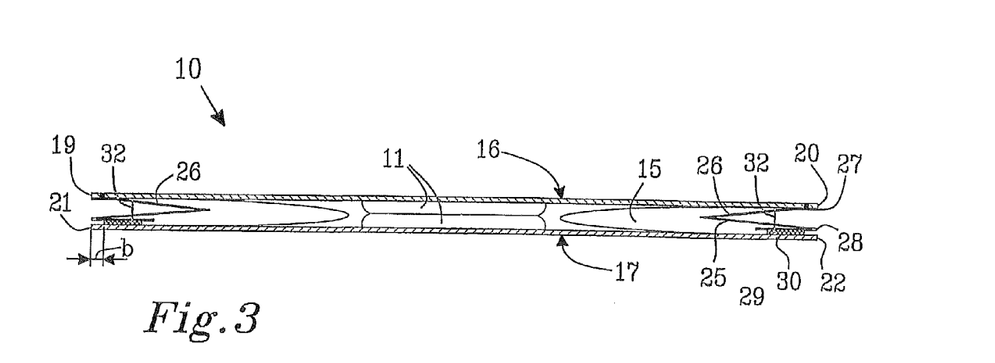
FIG. 3 is a cross-sectional view of the refastenable diaper according to the line III-III in FIG. 1 but shown in a position before use when the side panels are in a folded position.
Figure 4:
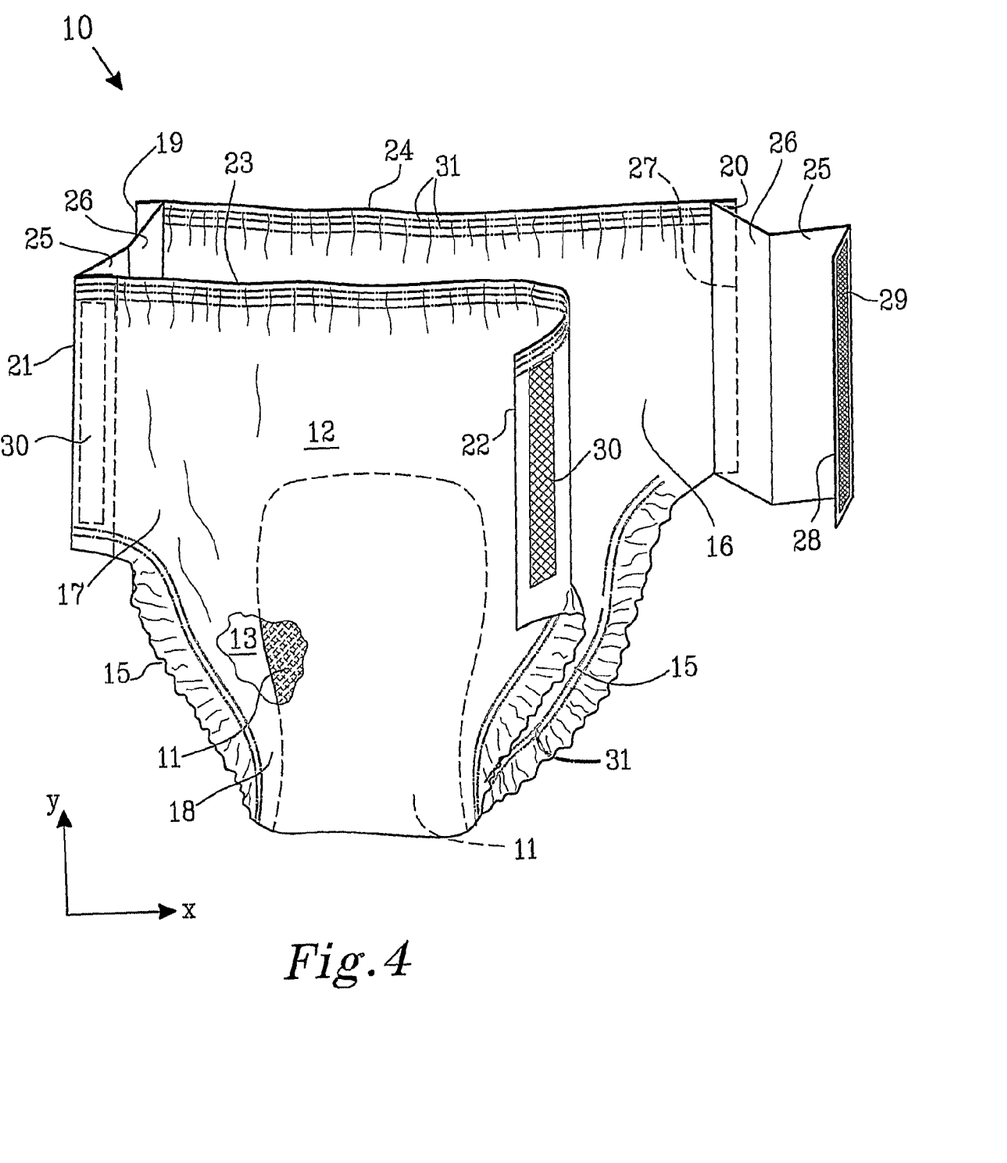
FIG. 4 shows the refastenable pant diaper according to FIG. 1 with one side panel opened.

The bridge members 26 are before use of the article configured in an accordion-like folded, for example Z-folded, position, as best illustrated in FIG. 3. This means that the articles may be packaged in a space-saving manner. The accordion-like folds may, before use of the article, be held together by easily breakable seals 32, for example ultrasonic point welds, thermobonding points or glue points. These seals 32 should be easily broken when the article is to be used.

When the article is taken out from the package for use the accordion-like folded bridge members 25 are unfolded and extended and will form side panels 25 bridging the first and second body panels 16 and 17.

The extension in transverse direction, x, of the bridge member 26 may vary depending on product type and size, but should preferably be at least 1 cm, preferably at least 2 cm and more preferably at least 3 cm as measured as the distance between the lateral edges 27 and 28.

The bridge member 26 has an extension in longitudinal direction, y, of the article of at least 75% of the length, a, of the respective second lateral edge 20 of the first body panel 16 near which it is attached, preferably at least 90% of said length and more preferably substantially equal to said length. The length, a, of the respective body panel refers to the distance between the waist opening 14 and the respective leg opening 15

The width of the second fastening member 30, as seen in the transverse direction, x, is at least 5 mm and no more than 40 mm. The length of the second fastening member 30, as seen in longitudinal direction, y, is at least 75% of the length, a, of the respective second lateral edge 20 of the first body panel 16 near which it is attached, preferably at least 90% of said length. It would be possible to have two or more second fastening members 30 arranged at short intervals along the respective first and second lateral edges 21, 22 of the body panel 17, wherein said length corresponds to the distance between the outer edges of the outermost second fastening members 30.

The second fastening member 21 is attached to the second body panel 17 immediately adjacent or at a short distance from the respective lateral side 21, 22 of the second body panel 17.

When opening the pant diaper the first and second fastening members 29 and 30 are separated from each other and may if desired be refastened again While it has been described and shown above that the refastenable fastening means are provided along both lateral sides of the pant diaper, it should be understood that only one side of the pant diaper may be provided with refastenable fastening means, while the opposite side edges of the first and second body panels may be fixedly attached to each other, such as by gluing or ultrasonic welding.

Figure 5:
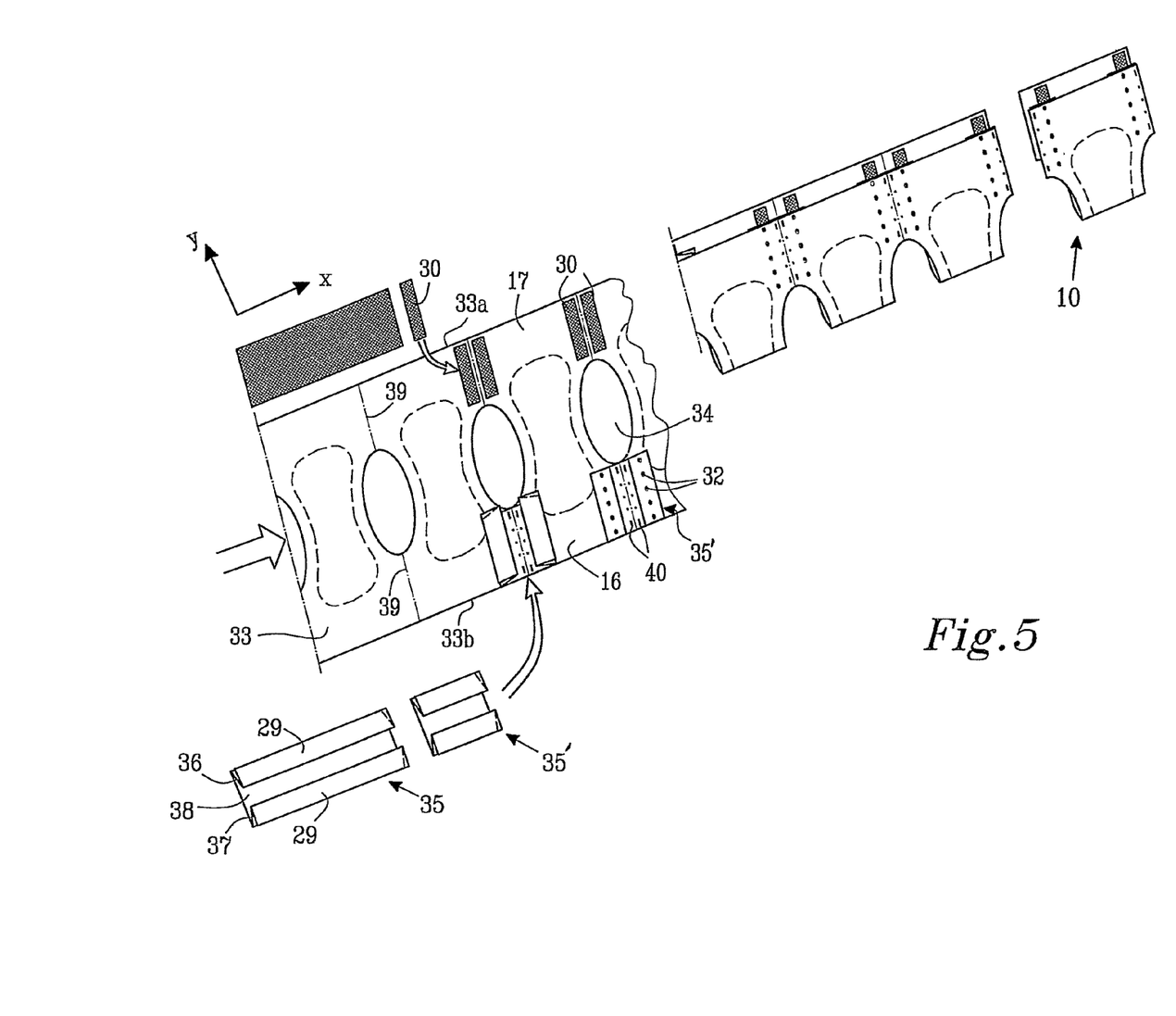
FIG. 5 illustrates schematically different manufacturing steps of one embodiment of making a refastenable pant diaper.

Referring to FIG. 5 an embodiment of a process for making the above described refastenable pant diaper is illustrated. Although the process is described in terms of different steps, it should be understood that it is a continuous process.

A continuous web of material 33 comprising a plurality of aligned absorbent article blanks aligned in a transverse direction (x), which will form the front, back and crotch panels of the pant diaper, is moved along a process line. The web 33 has longitudinal edges 33a and 33b. Holes 34 have been made in the web 33 (aligned blanks), which will form the leg openings 14 of the pant diaper. Absorbent cores 11, elastic members (not shown) etc. are also present with the blanks.

A web 35 of bridge forming material folded in an accordion-like fashion along each longitudinal edge is forwarded towards the web 33. The accordion-like folded portions 36 and 37 at either sides of the web 35 are formed as a mirror image to each other and are interconnected by a connecting portion 38. A first fastening member 29 is provided at each outer longitudinal side portion of the accordion-like folded portions 36 and 37. Alternatively at least a substantial portion of or even the entire accordion-like folded portions 36 and 37 as well as the connecting portion 38 may be of a material suited as first fastening member, for example a loop material for a hook-and-loop type fastener. The web 35 of bridge forming material is cut into lengths adapted to form a pair of bridge members 26 of adjacent article blanks.

The cut lengths 35' of bridge forming material is applied to the web 33 of aligned article blanks in the area between the hole 34 and one longitudinal edge 33b of the web 33, so that the connecting portion 38 between the two accordion-like folded portions 36 and 37 will bridge the intended line of separation 39 between two adjacent pant diaper blanks. The cut lengths 35' of wing-forming material are placed on the side of the blank that will form the body facing side, i.e. the inner coversheet. The cut lengths 35' of wing-forming material are applied in a position so that the accordion-like folds extend in a substantial longitudinal direction, y, of the articles to be formed from the blanks and are subsequently bonded to the blanks by gluing, ultrasonic bonding, thermobonding or the like, in an area 40 adjacent the intended line of separation 39. In an alternative embodiment a cut length 35' of bridge forming material is provided to each pant diaper blank on either sides of the intended line of separation. The accordion-like folded portions 36 and 37 will remain unbonded or may be temporarily bonded together by easily breakable seals, for example glue spots, ultrasonic welding spots or thermobonding spots, as mentioned above.

A web of second fastening member 30 is cut into desired lengths which are bonded to the web 33 of aligned blanks in the area between the hole 34 and the opposite longitudinal edge 33a of the web 33 at a selected distance from the intended line of separation 39. Alternatively the of second fastening member 30 is cut into lengths adapted to form second fastening members 30 for two adjacent pant diaper blanks, wherein each length is placed so as to bridge the intended line of separation 39 between two adjacent pant diaper blanks.

The web 33 of aligned blanks is subsequently folded in longitudinal direction to place the first fastening member 29 of each blank bonded to the first body panel in fastening contact with the second fastening member bonded to the second body panel of the same blank. The position of the first and second fastening members 29 and 30 should thus be adapted so that upon folding the web in longitudinal direction as shown in FIG. 5 the first and second fastening members 29 and 30 will be placed in fastening contact with each other.

The folded web of blanks is then cut along the intended line of separation 39 to form pant-like absorbent articles therefrom. In an alternative embodiment the web 33 of aligned blanks is cut along the intended lines 39 of separation before folding it. In another embodiment the holes 34 for forming the leg openings are cut after folding the web.

In a still further embodiment (not shown) both longitudinal edge portions of the cut lengths 35' of bridge forming material are fixedly attached to the respective side panel. In that case the first and second refastenable fastening members 29 and 30 are absent and the pant diaper is not refastenable. In other embodiments only one of the cut lengths 35' of bridge forming material for each article is refastenable, while the other bridge member has both longitudinal edge portions fixedly attached to the respective side panel. In still further embodiments both longitudinal edge portions of the bridge member is refastenably attached to the respective body panel.

Although only a few exemplary embodiments have been described in detail above, those skilled in the art will readily understand that many modification are possible and that any such modifications are intended to be included within the scope of this invention, which is defined in the following claims.

The invention claimed is:
1. A reclosable pant-type absorbent article comprising:
a longitudinal and a transverse axis;
a first body panel having a body facing side and a garment facing side;
a second body panel having a body facing side and a garment facing side, each body panel having first and second lateral edges,
said first and second body panels being interconnected by first and second side panels, at least one of said first and second side panels is releasably and refastenably attached to the first or second body panel,
the at least one side panel having a third lateral edge portion permanently attached to the body facing side of the first body panel, the third lateral edge portion having a terminal edge,
a fourth lateral edge portion of the at least one side panel releasably and refastenably attached to the body facing side of the second body panel, the fourth lateral edge portion having a terminal edge,
a first fastening member is arranged on said at least one side panel at or close to the fourth lateral edge portion thereof,
the third lateral edge portion of the at least one side panel is permanently attached to the first lateral edge portion of the first body panel so that the terminal edge of the third lateral edge portion faces a substantially same direction as that faced by a terminal edge of the first lateral edge of the first body panel, and
the fourth lateral edge portion of the at least one side panel is releasably and refastenably attached to the first lateral edge of the second body panel so that the terminal edge of the fourth lateral edge portion faces a direction substantially opposed to the direction faced by a terminal edge of the first lateral edge of the second body panel,
wherein a complementary second fastening member is arranged on the body facing side of the second body panel, said at least one side panel before use of the article being folded in an accordion-like fashion in the longitudinal direction of the article and is extended and unfolded when the article is worn.

2. An absorbent article according to claim 1, wherein the first and second fastening members are hook-and-loop type fasteners.

3. An absorbent article according to claim 2, wherein the first fastening member is of a loop material and the second fastening member comprises a hook material.

4. An absorbent article according to claim 1, wherein the at least one side panel before use is Z-folded.

5. An absorbent article according to claim 1, wherein at least a part of the at least one side panel is elastic.

6. An absorbent article according to claim 1, wherein the at least one side panel has an extension in the transverse direction of the article of at least 1 cm, as seen as the distance between its lateral edges.

7. An absorbent article as claimed in claim 1, wherein the at least one side panel has an extension in the longitudinal direction of the article of at least 75% of the length of the respective lateral edge of the first body panel near which it is attached.

8. An absorbent article as claimed in claim 2, wherein the second fastening member is attached to the second body panel at a distance of at least 2 mm inside the lateral side edge of said body panel.

9. An absorbent article as claimed in claim 2, wherein the width in the transverse direction of the second fastening member is at least 3 mm and the length in longitudinal direction is substantially equal to the length of the first fastening member.

10. An absorbent article as claimed in claim 2, wherein the entire at least one side panel is of a loop material.

11. An absorbent article as claimed in claim 1, wherein the accordion-like folds of the at least one side panel are held together, before the intended use of the article, by breakable seals.

12. A method of making side panels in a reclosable pant-like absorbent article, said article having a longitudinal and transverse direction, said method comprising:

aligning a plurality of article blanks in a transverse direction, each article blank including a first body panel and a second body panel, each body panel having first and second lateral edges, wherein adjacent blanks are joined between their first body panels and between their second body panels at intended lines of separation, said lines of separation coinciding with respective first and second lateral edges, said article blanks having a body facing side and a garment facing side in its intended use as absorbent article;

feeding a side panel forming material including a third lateral edge portion having a terminal edge and a fourth lateral edge portion having a terminal edge to each of the first body panels, to the intended body facing side thereof, said side panel forming material being folded in an accordion-like fashion, applying said side panel forming material to each of the first body panel with the accordion-like folds extending in a substantial longitudinal direction of the article, permanently bonding a portion of the side panel forming material to or adjacent the intended line of separation between adjacent first body panels so that the terminal edge of the third lateral edge portion of the side panel faces a substantially same direction as that faced by the lateral edge of the first body panel, while the rest of the accordion-like folded side panel forming material is left unbonded and arranged so that the terminal edge of the fourth lateral edge portion faces a direction substantially opposed to the direction faced by the terminal edge of the third lateral edge position, said unbonded portion having a longitudinal edge portion;

attaching a first fastening member of a refastenable fastening means to the fourth lateral edge portion of the accordion-like folded side panel forming material;

bonding a second fastening member of said refastenable fastening means to the second body panel of each article blank to the intended body side thereof;

folding the article blanks along a central transverse folding line so that the first fastening member is brought in contact with the second fastening member bonded to the second body panel of the same blank to provide a refastenable bonding of the accordion-like folded bridge forming material to the second body panel;

cutting the folded blanks along the intended line of separation to form pant-like absorbent articles therefrom; or cutting the blanks along the intended lines of separation before folding them.

13. The method as claimed in claim 12, wherein said web of side panel forming material is provided with two accordion-like folded portions being the mirror image of each other and being interconnected by a connecting portion, bonding said connecting portion to adjacent first body panels on either sides of the intended line of separation there between, so that after cutting along the intended line of separation, the connecting portion will be cut thus leaving each first body panel with an accordion-like folded portion attached thereto.

14. The method as claimed in claim 12, further comprising bonding the accordion-like folds together by breakable seals.

15. An absorbent article according to claim 1, wherein the side panel has a front face and a rear face, wherein the front face of the side panel is attached facing one of the first or second body panels and the second face of the side panel is attached facing the other of the first or second body panel.

* * * * *